(12) United States Patent
Laniauskas et al.

(10) Patent No.: US 9,890,353 B2
(45) Date of Patent: Feb. 13, 2018

(54) MEDIA SUCTION DEVICES AND METHODS

(71) Applicant: Janssen Biotech, Inc., Horsham, PA (US)

(72) Inventors: Daina Laniauskas, Raritan, NJ (US); Joseph Hammer, Raritan, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 542 days.

(21) Appl. No.: 14/204,363

(22) Filed: Mar. 11, 2014

(65) Prior Publication Data

US 2014/0261706 A1 Sep. 18, 2014

Related U.S. Application Data

(60) Provisional application No. 61/794,356, filed on Mar. 15, 2013, provisional application No. 61/841,713, filed on Jul. 1, 2013.

(51) Int. Cl.
*G01N 1/12* (2006.01)
*C12M 1/00* (2006.01)
*G01N 1/14* (2006.01)
*B01D 17/02* (2006.01)

(52) U.S. Cl.
CPC ......... *C12M 29/00* (2013.01); *B01D 17/0214* (2013.01); *G01N 1/12* (2013.01); *G01N 1/14* (2013.01); *G01N 2001/1418* (2013.01); *Y10T 137/0318* (2015.04); *Y10T 137/8593* (2015.04)

(58) Field of Classification Search
CPC .................................................... C12M 29/00
USPC ........................................................ 436/177
See application file for complete search history.

(56) References Cited

U.S. PATENT DOCUMENTS

| 991,657 | A | 5/1911 | Sekine |
| 1,445,527 | A | 2/1923 | Maier |
| 2,161,151 | A | 6/1939 | Freedman |
| 3,172,235 | A * | 3/1965 | Bjorklund ............. C12M 41/00 435/286.5 |
| 5,304,303 | A | 4/1994 | Kozak, III |
| 6,592,751 | B2 | 7/2003 | Haridas |
| 8,337,700 | B1 | 12/2012 | Zuk, Jr. |
| 2003/0001161 | A1 | 1/2003 | Ota et al. |
| 2011/0117650 | A1 | 5/2011 | Riordan |

FOREIGN PATENT DOCUMENTS

EP 1696024 A1 8/2006

OTHER PUBLICATIONS

Kathleen A. Pennington, Jessica M. Schlitt, Laura C. Schulz "Isolation of Primary Mouse Trophoblast Cells and Trophoblast Invasion Assay" J. Vis. Exp. (59), e3202, DOI : 10.3791/3202 (2012).*
Tissue Culture: Methods and Applications, edited by Paul F. Jr. Kruse, 1973 (pp. 227 and 228 attached).*

* cited by examiner

*Primary Examiner* — Christopher Adam Hixson
*Assistant Examiner* — Emily R. Berkeley
(74) *Attorney, Agent, or Firm* — Lois A. Granneschi

(57) ABSTRACT

Devices and methods are provided for removing media from a culture vessel that decreases disruption of the interface between the cellular material and media within the vessel such that aspiration and removal of cells or cell clusters along with the media is minimized. In addition, the media fluid turbulence is decreased so as to minimize the activation or disruption of cells and cell clusters.

14 Claims, 5 Drawing Sheets

MEDIA SUCTION DEVICES AND METHODS

CROSS-REFERENCE TO RELATED APPLICATIONS

This application claims priority to U.S. Provisional Application No. 61/794,356, filed on Mar. 15, 2013, and U.S. Provisional Application No. 61/841,713, filed on Jul. 1, 2013, the disclosures of which are incorporated by reference herein in their entireties.

FIELD OF THE INVENTION

The present invention generally relates to the field of apparatuses and methods used for culturing cells. More specifically, the invention discloses apparatuses and methods for removing media from cell culture containers.

BACKGROUND

Culture vessels, meaning containers for use in culturing cells and tissue growth, are well known. During typical growth or differentiation of cells, cells exhaust nutrients found in their growth media while simultaneously producing metabolic byproducts. Highly metabolic cell cultures may require replacement of the spent media with fresh media on a daily or bi-daily basis in order to replace nutrients and rid the culture of the byproducts.

A common approach for separating spent media involves first settling the cells, cells clusters, or micro-carriers to which the cells or cell clusters are attached to the bottom of the culture vessel. The spent media is then removed via suction or pumping through a straight tube with a hole at the distal-most end thereof, known as a diptube, submerged in the spent media using a pump. The goal of the process is to remove at least about 90% of the spent media, while removing as few cells as possible.

However, suctioning out of the media causes an upward pull directly above the settled cell layer. Additionally, an increase in pumping rate results in an increased pulling force above the cell layer. Thus, fast pump rates can disrupt the settled cell layer resulting in re-suspension of cell clusters, which re-suspended clusters are more likely to be removed as waste along with the spent media.

While fast pump rates may lead to the unintended removal of cells and cell clusters, pumping the media at too slow of a rate also can negatively impact the settled cell layer. Unlike cells in suspension, settled cells are in very close contact with each other and, when kept in a settled phase for a period of time, cell clusters may fuse to form larger cluster aggregates. Clusters with diameters larger than 200 μM may begin to experience gas and nutrient transport limitations. As a result, a sub-optimal differentiation or even cell death may be observed.

BRIEF DESCRIPTION OF THE DRAWINGS

For the purpose of illustrating the invention, the following figures demonstrate embodiments of the present invention. It is to be understood, however, that the invention is not limited to the precise arrangements, examples, and instrumentalities shown.

DETAILED DESCRIPTION OF THE INVENTION

The invention is directed to devices and methods for removing media or other matter from a culture vessel for cell culturing or tissue growth with minimal disruption of the cells or tissue. The devices and methods of the invention remove media from the container such that only about 10% or less of the cells or cell clusters within the container are removed along with the media. In addition, the devices and methods minimize the media fluid turbulence thereby minimizing the cell aggregation or fusion as well as disruption of the cells and cell clusters.

In one embodiment, the invention provides a method of removing media from a culture vessel containing cellular material and a media comprising, consisting essentially of, and consisting of the steps of settling the cellular material to the bottom of the container; providing a suction device having a proximal portion and a distal portion, the distal portion including at least one opening; submerging the distal end of the suction device into the media in the container to a depth determined by the position of the at least one opening; and suctioning media through the at least one opening of the suction device and out of the culture vessel. For purposes of the invention, by "cellular material" is meant one or more of cells, cell clusters, and tissue.

In another aspect of the invention, a device is provided for removing media from a culture vessel comprising, consisting essentially and consisting of a hollow tube having a proximal and a curved distal portion, the curved distal portion comprising at least one opening.

Figure 1:
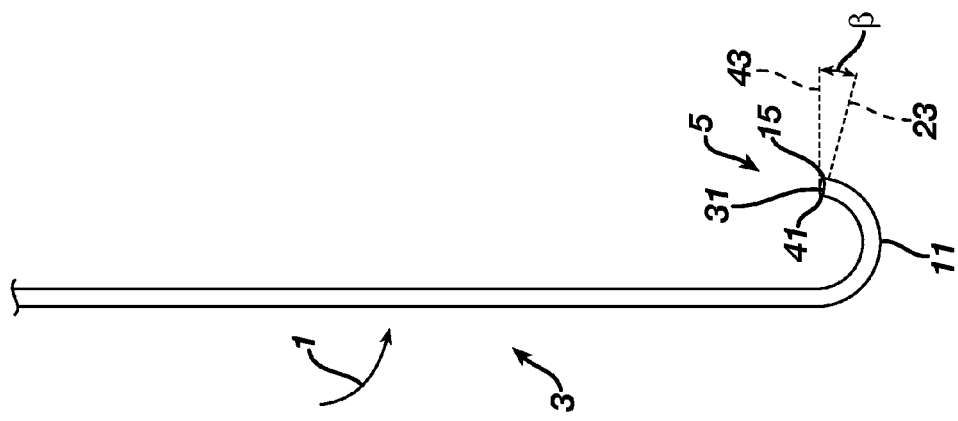
FIG. 1 is a side view of an embodiment of a media suction device of the invention.
Figure 2:
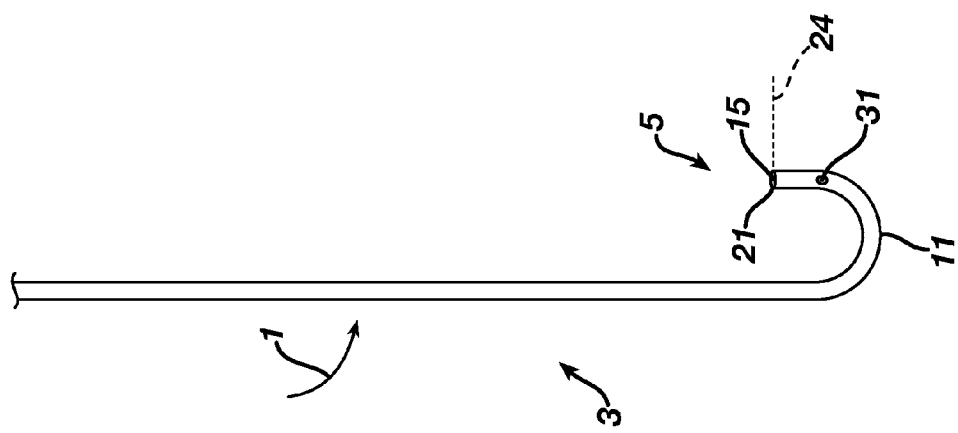
FIG. 2 is a side view of an embodiment of a media suction device of the invention.
Figure 3:
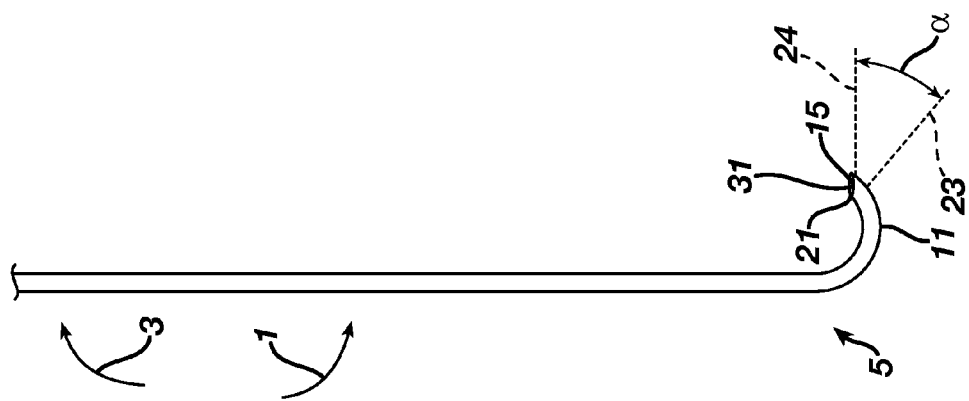
FIG. 3 is a side view of an embodiment of a media suction device of the invention.

Referring now to FIGS. 1 through 3, device 1 is shown with a proximal portion 3 and a distal portion 5. In relation to the device, by "proximal" is meant the end of the device in closest proximity to the suctioning device that connects to device 1 and provides suctioning force and by "distal" is meant the portion of the device farthest from the suctioning device. As shown, device 1 is formed from hollow tubing and, preferably, has substantially constant inner and outer diameters. The device may be formed from any suitable medical grade material including, without limitation, stainless steel, polymers and combinations thereof. If it is desired that the device be re-usable, the material must also be able to withstand sterilizing conditions such as one or more of heat and radiation. The length and inner and outer diameters of the device are selected based on the size of the culture vessel in use and so as to keep any disturbance of the vessel culture system dynamics by the device's use to a minimum.

The proximal portion 3 may be, and preferably is, a substantially straight, elongated section. Distal portion 5 preferably has a curved section 11 with a distal-most end 15. The curved portion may be of any suitable curvature. However, the curvature is preferably selected to minimize turbulent flow within the device during suctioning. Distal-most end 15 may be formed with a substantially horizontal face 21 at an angle α formed between a first line 24 extending from horizontal face 21 and a second line 23 extending perpendicular to the cross-section of the curved section 11.

Referring to FIG. 2, alternatively distal-most end 15 may terminate at substantially horizontal face 21 with no angle between the horizontal face 21 of the distal end 15 meaning that, in comparison with the embodiment of FIG. 1, the angle α may is zero. At least one opening 31 is included either at distal-most 15, as shown in FIGS. 1 and 3, or along curved section 11 as shown in FIG. 2. The position of opening 31 determines the height of the media that will remain in the culture vessel after suctioning is complete. Thus, the depth to which device 1 will be submerged in the media with in a culture vessel will be determined by the location of the at least one opening 31. Preferably, the at least one opening 31 is positioned slightly away from the apex of the curvature of curved section 11 to maximize the amount of growth media suctioned and to minimize suctioning or disruption of the cellular material. Disruption or agitation to the cells also may be minimized by positioning the at least one opening 31 so that it faces away from the cellular material layer and the suction force applied via the device is not directly facing the layer.

As yet another alternative, and with reference to FIG. 3, the distal-most end 15 may be formed with perpendicular face 41, which is perpendicular to the cross-section of the curved section 11. The perpendicular face 41 may form an angle β between a horizontal reference plane 43, such as along an axis perpendicular to the longitudinal axis of proximal portion 3, and a second line 23.

Figure 4:
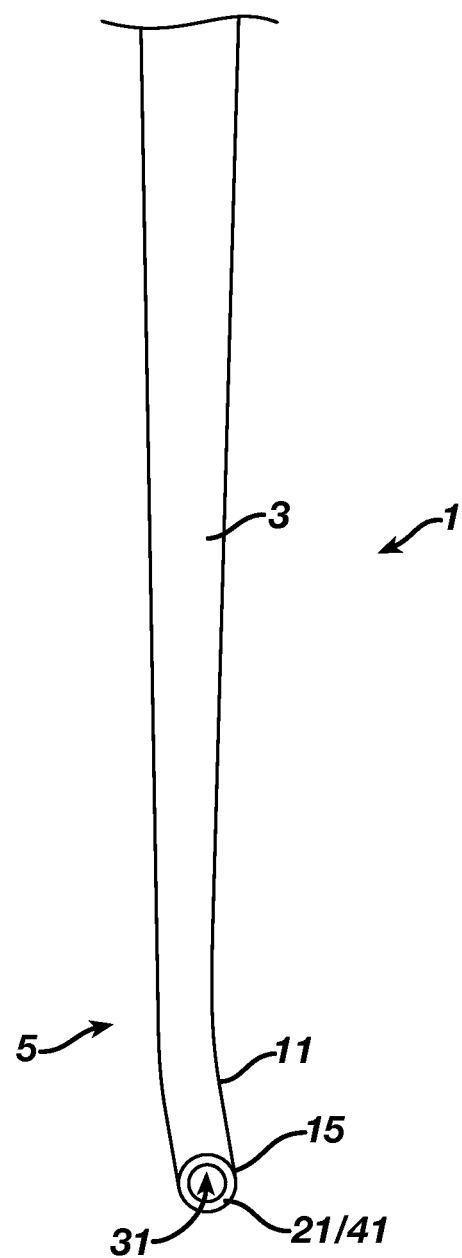
FIG. 4 is a front view of an embodiment of a media suction device of the invention.

Referring to FIG. 4, a view of distal-most end 15 of an embodiment of device 1 is shown with at least one opening 31 at distal-most end 15. The inner diameter may be, and preferably is, substantially constant through both the upper and lower portions 3 and 5 of device 1.

Figure 5:
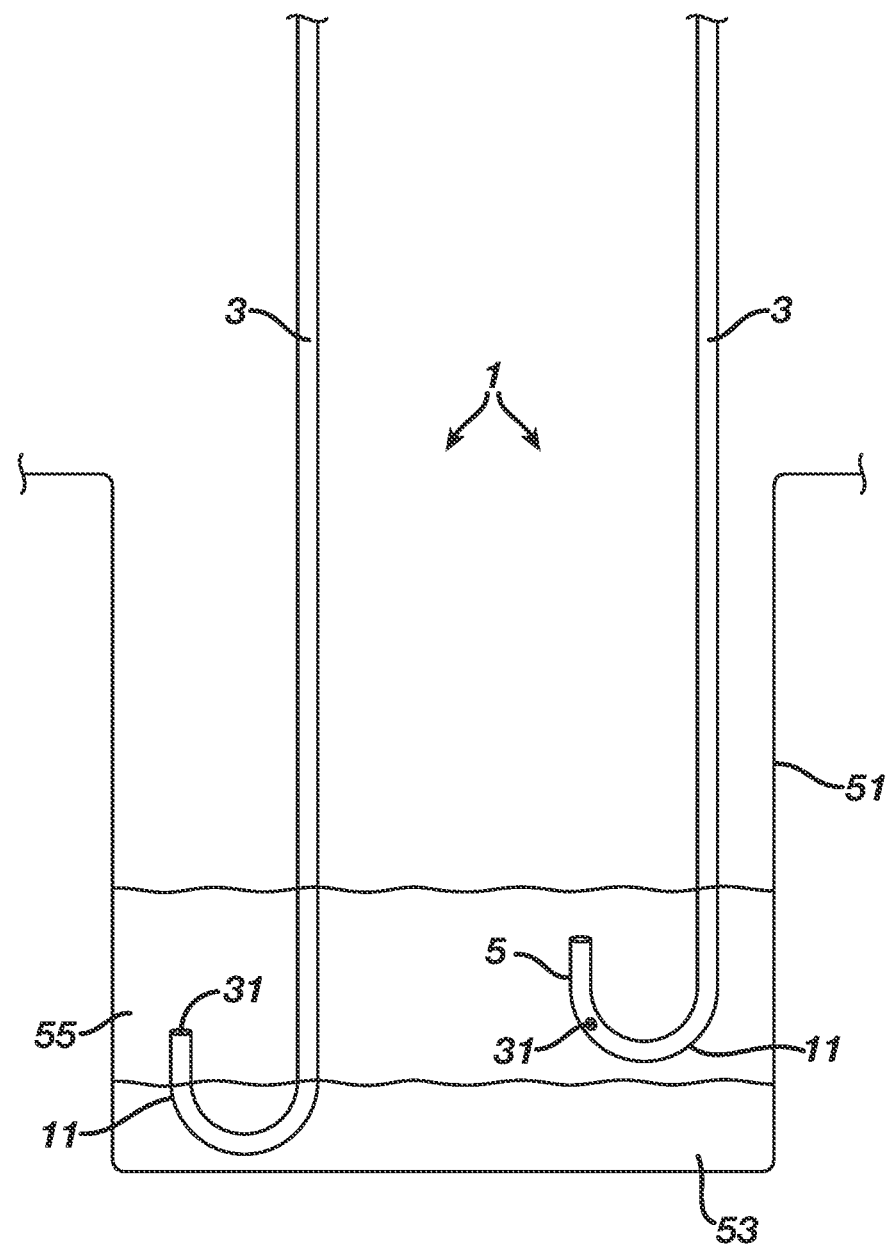
FIG. 5 is a side view of exemplary positions of two media suction devices of the invention in a culture vessel.

In FIG. 5, an embodiment of the device 1 inserted into a culture vessel 51 is shown. By "culture vessel" is meant a container useful for cell culturing or tissue growth. Such containers include bioreactors, flasks (such as T-Flasks, hyperFlasks, spinner flasks, Erlenmeyer flasks, and the like), stainless steel, glass, and plastic tank-type vessels. The device may be held within the vessel by any suitable attachment to the vessel including, without limitation, by a compression fitting into a head plate attached to the vessel (not shown). The manner of attachment will depend upon the type and size of the vessel used. As shown, cellular material layer 53 and growth media 55 are seen. In use of the device, the cellular material layer 53 is allowed to settle or precipitate to the bottom of the vessel 51. The amount of time required for settling will depend on the size of the vessel, the amount and type of media used, the amount of cells within the vessel, the size and specific gravity of cellular material within the vessel, and the size and specific gravity of any micro-carriers used. The distal portion 5 and curved section 11 of media suction device 1 are submerged in the growth media 55. Two exemplary positions of device 1 are shown in FIG. 5. As shown, the curved section 11 may be submerged in the cellular material layer 53 provided that the at least one opening 31 extends above the cellular material layer 53. Preferably, curved section 11 and opening 31 are located above the settled cellular material layer 53.

In order to remove growth media 55 from the culture vessel 51, a suction force is applied to the proximal end of the device 1. The suction force may be applied by any suitable equipment including a pump or a vacuum. As suction is applied to the device 1, growth media 55 enters the at least one opening 31 of the device 1. The suction force applied and time for suctioning will be determined by a consideration of the length and inner diameter of device 1, the size of the culture vessel, the amount of media to be suctioned, the density of the media to be suctioned, the thickness of the settled cellular material layer, the size and specific gravity of cell clusters within the vessel, and the size and specific gravity of any micro-carriers used. The suctioning process preferably results in a removal of at least 90% of the spent media, while removing as little of the cellular material as possible. Although fast suctioning rates and high suction force may lead to unintended removal of cell clusters, too slow of a rate and force can also have a negative impact on the resulting cell population because the settled cells are in very close contact with each other. When kept in a settled phase for a period of time, cell clusters may fuse to form larger cluster aggregates. Clusters with diameters larger than 200 μM may begin to experience gas and nutrient transport limitations. As a result, sub-optimal differentiation or cell death may be observed.

Figure 6:
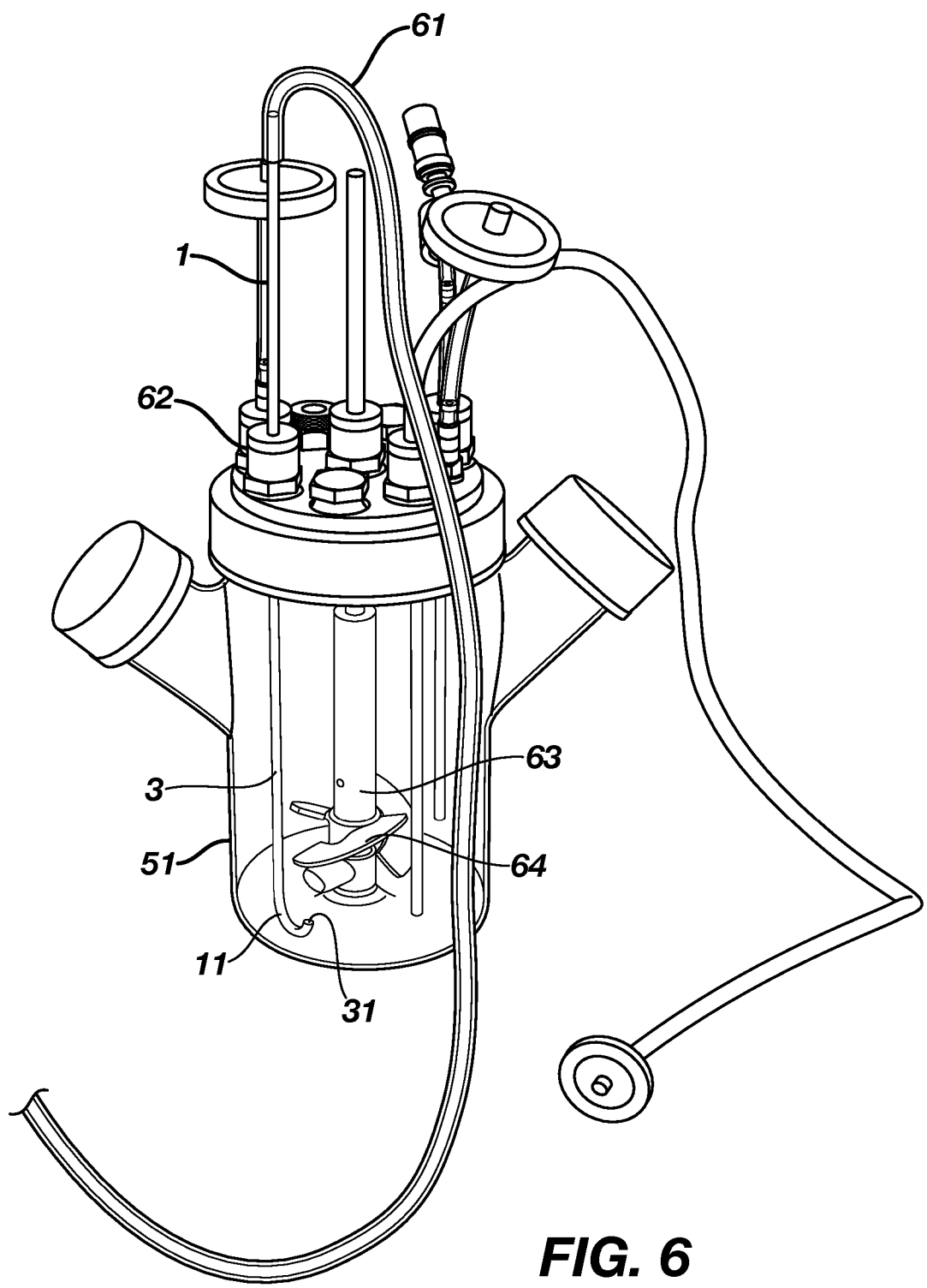
FIG. 6 is an exemplary view of a media suction device of the invention in a culture vessel.

In FIG. 6 is shown a representative culture vessel incorporating the device of the invention. The vessel shown is used for culturing cells or tissue, for example, pluripotent stem cells in dynamic suspension, and has an internal surface designed such that pluripotent stem cells cultured therein are unable to adhere or attach to such a surface (e.g., non-tissue culture treated cells, to prevent attachment or adherence to the surface). Vessel 51 includes device 1 with suction hose 61 extending from the proximal end thereof. Device 1 is attached to vessel 51 by compression fitting 62. Also shown, is an agitator, which may be, for example, an impeller shaft and blade, 63 and 64, respectively, that provides agitation to the media and cells.

The invention will be further clarified by a consideration of the following, non-limiting examples.

EXAMPLES

Example 1

In this example, the maximal pump rate of some embodiments of the devices of the invention are determined. The "maximal pump rate" is defined as the fastest rate spent media may be pumped, or suctioned, out of a reactor during a media exchange without disrupting the settled cellular material layer. Clusters from pluripotent human embryonic stem cell line H1 (NIH code: WA01, WiCell Research Institute, Madison, Wis.), with an average diameter of 150 μM (range 100-200 μM), were transferred to a 500 mL bioreactor (catalog #DS0500TPSS, DASGIP Information and Process Technology, Juelich, Germany ("DASGIP")) at a target cell density of 0.9 million/mL (range 0.8-1.2 million/mL) in a medium containing 2% BSA (Proliant, Inc., Boone, Iowa) and were used to assess maximal pump rates of various media suction devices.

The 500 mL glass reactor's headplate (Catalog #77101001, DASGIP) was set up to include four, 4 mm OD single port compression fittings (Catalog #78532282, DASGIP). The first single port was fitted with a straight barbed diptube, (4 mm OD 2 mm ID, 225 mm length) (Catalog #78107023, DASGIP) and set-up to allow for sampling the reactor for counting purposes. A 2.5 inch long piece of 2 mm ID/5.2 mm OD platinum cured silicone (Catalog #96420-14, Cole-Parmer North America, Vernon Hills, Ill.) was attached to the barbed end of the sampling diptube. The silicone tubing was then threaded with a small pinch tubing clamp. The open tubing end was fitted with a PVDF female luer×

3/32" hose barb (Catalog #45501-02, Cole-Parmer) connected to a swab-able polycarbonate, silicone valve (Catalog #245204024, Halkey-Roberts Corporation, Saint Petersburg, Fla.). The sampling diptube was inserted into the reactor such that the distal opening was approximately even with the center of the pitch blade impeller (Catalog #78100576, DASGIP) and the compression fitting was tightened to hold its place. The other 3 single port compression fittings were fitted with tubes for testing maximal pump rates: (1) a standard, straight diptube with an opening at the distal-most end ("Standard"); (2) a device of the invention with a wholly straight configuration and with the opening located several millimeters from its distal-most end ("Straight"); and (3) a device of the invention as shown in FIG. 2, but with the opening at the distal-most end (as shown in FIG. 1) ("Curved"). The inner diameter and outer diameter of each of the tubes was 2 mm and 4 mm. Each was inserted into the reactor such that the distal opening would allow for 90% of the media thereby leaving behind 50 mL of spent media in the vessel containing the cell aggregates. A 24 inch piece of 1/8 inch ID, 1/4 inch OD C-FLEX® tubing, a heat sealable thermoplastic elastomer (Catalog #06422-05, Cole-Parmer media of the three tubes. This C-FLEX® tubing was then welded to a pump tubing assembly, which included a size 25 masterflex pump tubing section flanked by 12 inch C-FLEX® pieces. A 500 mL media transfer bottle (CAP2V8®, Sanisure, Inc. Indianapolis, Ind.) was welded to the other end of the pump tubing assembly into which spent media was to be pumped.

The bioreactor was then moved to a magnetic stirplate (DASGIP) and the agitation was turned to 70 RPM. The cells were allowed mix for 10 minutes, at which point a homogenous mixture of cell clusters in media was observed. One 1.5 mL flush sample and three 2 ml count samples were then pulled from the bioreactor using 3 mL luer lock syringes (Catalog #301073, Becton, Dickinson and Company, Franklin Lakes, N.J.) via the swab-able valve of the sample port described above. The total cell density of each sample was determined using the NUCLEOCOUNTER® NC-100™, a cell counter (ChemoMetec A/S, Allerod, Denmark). After ensuring the cell density fell within specifications, the agitation was turned off and the cells proceeded to settle to the bottom of the vessel for approximately 5 minutes. During this time, the pump tubing corresponding to the standard diptube was properly inserted into the peristaltic pump (Model #7551-00, Cole-Parmer). At the 5 minute mark, the peristaltic pump was turned on at a rate of 10 RPM. The rate of pumping was slowly increased by about 10 RPM every 5 seconds until a visual disruption of the settled cellular material layer was observed. The maximal pump rate was denoted as the fastest speed which could be used in combination with a particular tube or device, without visualizing any disruption in the cellular material layer. Once a maximal pump rate was established, the media was returned to the reactor and the agitation was re-started. The experiment was repeated for each tube type. Maximal pump rates and corresponding volumetric flow rates are listed below.

| Diptube Specification | Maximal Pump Rate (RPM) | Maximal Pump Rate (mL/min) |
|---|---|---|
| Standard | 35 | 58.3 |
| Straight | 40 | 66.7 |
| Curved | 70 | 116.7 |

From these values, the time to remove 450 mL of media from a 500 mL reactor and 1800 mL from a 3 L reactor (2 L w/v) were calculated below.

| Diptube type | Maximal Pump Rate (mL/min) | Time to remove 450 mL (mins) | Time to remove 1800 mL (mins) |
|---|---|---|---|
| Standard | 58.3 | 7.7 | 25.7 |
| Straight | 66.7 | 6.7 | 22.5 |
| Curved | 116.7 | 3.9 | 12.9 |

As compared to the Standard tube, the Straight and Curved devices of the invention allow for a higher maximal pump rate, with the Curved tube demonstrating superior performance providing a faster rate of media exchange and minimizing cluster to cluster contact time.

Example 2

Clusters from pluripotent human embryonic stem cell line H1 (NIH code: WA01), with an average diameter of 150 μM (range 100-200 μM), were transferred to a 500 mL bioreactor (catalog # DS0500TPSS, DASGIP) at a target cell density of 0.9 million/mL (range 0.8-1.2 million/mL) in 500 mL (450-520 mL) of MCDB131 containing 2% BSA (Proliant). The 500 mL glass reactor's headplate (Catalog #77101001, DASGIP) was set up to include three, 4 mm OD single port compression fittings (Catalog #78532282, DASGIP). The first single port was fitted with a standard straight 4 mm OD, 2 mm ID, 225 mm length stainless steel diptube (Catalog #78107023, DASGIP). A 2.5 inch long piece of 2 mm ID/5.2 mm OD platinum cured silicone (Catalog #96420-14, Cole-Parmer) was attached to the barbed end of this sampling diptube. The silicone tubing was then threaded with a small pinch tubing clamp. The open tubing end was fitted with a PVDF female luerx3/32" hose barb (Catalog #45501-02, Cole-Parmer) connected to a swabable polycarbonate, silicone valve (Catalog #245204024, Halkey-Roberts). The sampling diptube was inserted into the reactor such that the distal opening was approximately even with the center of the pitch blade impeller (Catalog #78100576, DASGIP,) and the compression fitting was tightened to hold its place. Of the remaining single port compression fittings, one was fitted with a standard ("Standard"), straight diptube as described in Example 1 while the other was fitted with a curved design of the invention ("Curved") also as described in Example 1. The Standard and Curved tubes were inserted into the reactor such that the distal opening would allow for allow for 90% of the media, leaving behind 50 mL of spent media in the vessel containing the cell aggregates during a media exchange. To the proximal end of each media exchange diptube a 24 inch piece of C-FLEX® tubing was attached. The C-FLEX® tubing was then welded to a pump tubing assembly, which included a size 25 masterflex pump tubing section flanked by 12" C-flex pieces. A 500 mL media transfer bottle (CAP2V8®, SaniSure) was welded to the other end of the pump tubing assembly into which spent media would be pumped.

Prior to initiating the media exchange, the cell density within the vessel was determined by withdrawing one 1.5 mL flush sample and 4×2 mL samples for cell counting purposes using 3 mL luer-lock syringes (Catalog #301073, Becton-Dickinson) through the sampling diptube swabable valve. Total cell counts were determined using the NUCLEOCOUNTER® NC-100™, a cell counter (ChemoMetec). After the counts were obtained, the agitation was turned off and the cells were allowed to settle for 5 minutes. During this time, the pump tubing connected to the test diptube was inserted into the peristaltic pump (Model #7551-00, Cole-Parmer). At the end of 5 minutes, the peristaltic pump was turned on at a constant rate of 70 RPM (116 mL/min) and the spent media was removed until only air ran through the C-FLEX® line, thereby leaving 50 mL of residual media and cells in the vessel. Once the spent media was removed, the agitation was re-engaged and a fresh bottle containing media (MCDB131+2% BSA) was then welded onto the pump tubing assembly and added to the reactor.

The spent media was transferred into two 175 mL conicals (Catalog #3145-0175, Thermo Fisher Scientific, Waltham, Mass.) and centrifuged for 1200 RPM/5 mins. After the supernatant was discarded, the cell pellets were combined and a total cell count was obtained using the nucleocounter. This count was denoted as the number of cells removed during media exchange. Using the gathered data, the percentage of cells lost was calculated by comparing the total cells removed during the media exchange to the total cells present prior to the exchange. The experiment was repeated 5 times per tube and the average results are shown below. After media removal completed by the Standard tube, an area of approximately 1 $cm^2$ area can be visualized completely devoid of cells. No such regions are observed when the Curved tube is used.

Figure 7:
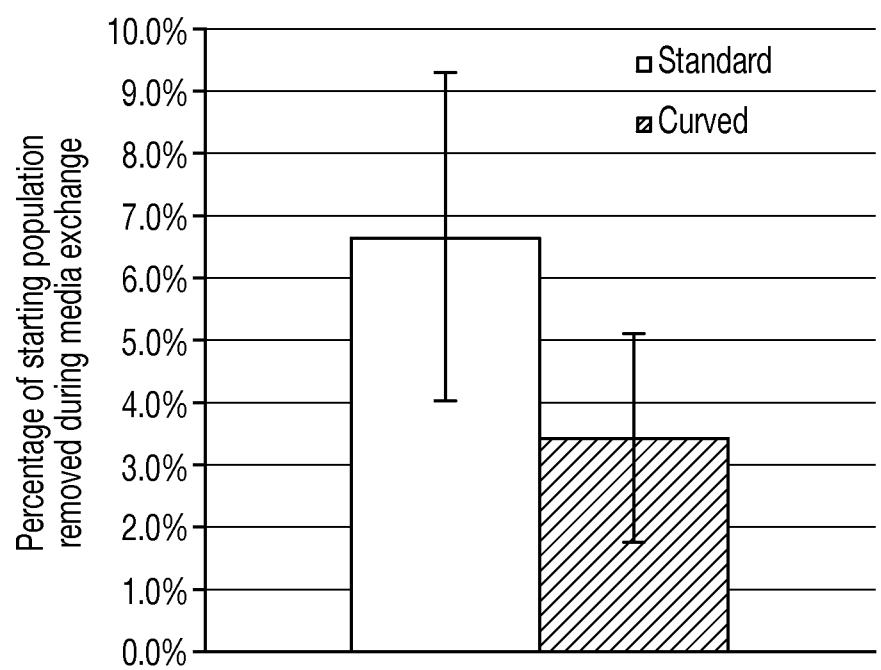
FIG. 7 is a graph comparing the results of using a prior art, or standard, diptube and a media suction device of the invention.

On average, a media exchange completed with the Curved tube removed approximately half as many cells as compared to a standard Standard tube as shown in the plot in FIG. 7. An independent sample Student's t-test showed that the difference in percentage of cells lost during a media exchange completed with the Standard tube (M=6.67, SD=2.64) and the Curved tube (M=3.43, SD=1.68) were statistically significant (t (8)=2.32, $p<0.05$).

While the invention has been described and illustrated herein by references to various specific materials, procedures and examples, it is understood that the invention is not restricted to the particular combinations of material and procedures selected for that purpose. Numerous variations and modifications of such details can be implied as will be appreciated by those skilled in the art. Moreover, features described in connection with one embodiment of the invention may be used in conjunction with other embodiments, even if not explicitly stated above. It is intended that the specification and examples be considered as exemplary, only, with the true scope and spirit of the invention being indicated by the following claims. All references, patents, and patent applications referred to in this application are herein incorporated by reference in their entirety.

We claim:

1. A method of removing media from a culture vessel containing a cellular material and a culture media, the method comprising:
    allowing the cellular material to settle to the bottom of the culture vessel;
    providing a suction device having:
        a proximal portion defining a longitudinal axis, and
        a distal portion having a curved section defining an arc and a terminal section having an opening therein;
    submerging the distal portion of the suction device into the vessel such that the opening is in the media; and
    suctioning media through the opening;
    wherein the arc is defined starting from the longitudinal axis of the proximal portion and is greater than 90°; and
    wherein the opening on the terminal section is oriented in the direction of the longitudinal axis to minimize disruption of the settled cells.

2. The method of claim 1, wherein 10% or less of the cellular material within the culture vessel is removed along with the culture media.

3. The method of claim 1, wherein the suction device comprises a second opening.

4. The method of claim 3, wherein the second opening is in the curved section.

5. The method of claim 1, wherein the suction device has a maximal pump rate between 40-70 RPM.

6. The method of claim 1, wherein the suction device has a maximal pump rate between 66-117 mL/min.

7. The method of claim 1, wherein the suction device has a maximal pump rate of 70 RPM.

8. The method of claim 1, wherein the suction device has a maximal pump rate of 117 mL/min.

9. The method of claim 1, wherein the terminal section extends beyond the curved section.

10. The method of claim 9, wherein the terminal section is parallel to the longitudinal axis.

11. The method of claim 10, wherein the suction device comprises a second opening in the terminal section.

12. A method of removing media from a culture vessel containing a cellular material and a culture media, the method comprising:
    allowing the cellular material to settle to the bottom of the culture vessel;
    providing a suction device having:
        a proximal portion defining by a longitudinal axis, and
        a distal portion having a curved section defining an arc and a terminal section having an opening therein;
    submerging the distal portion of the suction device into the vessel such that the at least one opening is in the culture media; and
    suctioning media through the opening;
    wherein the arc is defined starting from the longitudinal axis of the proximal portion and is greater than 90°; and
    wherein the opening on the terminal section is not oriented in the direction of the longitudinal axis to minimize disruption of the settled cells.

13. The method of claim 12, wherein the suction device comprises a second opening in the terminal section.

14. The method of claim 12, wherein 10% or less of the cellular material within the culture vessel is removed along with the culture media.

* * * * *